United States Patent
Den Brinker et al.

(10) Patent No.: US 12,102,472 B2
(45) Date of Patent: Oct. 1, 2024

(54) DETECTING SUBJECTS WITH DISORDERED BREATHING

(71) Applicant: KONINKLIJKE PHILIPS N.V., Eindhoven (NL)

(72) Inventors: Albertus Cornelis Den Brinker, Eindhoven (NL); Okke Ouweltjes, Veldhoven (NL); Koray Karakaya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 792 days.

(21) Appl. No.: 17/042,525

(22) PCT Filed: Mar. 20, 2019

(86) PCT No.: PCT/EP2019/056923
§ 371 (c)(1),
(2) Date: Sep. 28, 2020

(87) PCT Pub. No.: WO2019/185414
PCT Pub. Date: Oct. 3, 2019

(65) Prior Publication Data
US 2021/0007704 A1    Jan. 14, 2021

(30) Foreign Application Priority Data
Mar. 28, 2018  (EP) .................................... 18164468

(51) Int. Cl.
*A61B 5/08*      (2006.01)
*A61B 5/00*      (2006.01)
(Continued)

(52) U.S. Cl.
CPC ............ *A61B 7/003* (2013.01); *A61B 5/0816* (2013.01); *A61B 5/4818* (2013.01);
(Continued)

(58) Field of Classification Search
CPC ......... A61B 5/08; A61B 5/7246; A61B 7/003; A61B 5/0816; A61B 5/4818;
(Continued)

(56) References Cited

U.S. PATENT DOCUMENTS

| | | | |
|---|---|---|---|
| 6,213,955 B1 * | 4/2001 | Karakasoglu ........ | A61B 5/6814 128/204.23 |
| 11,712,198 B2 * | 8/2023 | Dafna .................. | A61B 5/7264 600/586 |

(Continued)

FOREIGN PATENT DOCUMENTS

| | | | | |
|---|---|---|---|---|
| CN | 110113998 A | * | 8/2019 | ........... A61B 5/4806 |
| CN | 110234279 A | * | 9/2019 | ........... A61B 5/4818 |
| WO | WO-2018011801 A1 | * | 1/2018 | ........... A61B 5/0816 |

OTHER PUBLICATIONS

International Search Report Jun. 13, 2019.
(Continued)

*Primary Examiner* — Navin Natnithithadha

(57) ABSTRACT

There is provided an apparatus (100) for detecting subjects with disordered breathing. The apparatus (100) comprises one or more processors (102) configured to acquire an acoustic signal from an acoustic sensor (108) in an environment, determine a plurality of acoustic signal components from the acquired acoustic signal and determine a plurality of signal envelopes or energy signals based on the acoustic signal components. One or more processors (102) are also configured to analyze the determined plurality of signal envelopes or energy signals to detect whether there are one or more subjects in the environment with disordered breathing.

13 Claims, 4 Drawing Sheets

(51) Int. Cl.
  *A61B 7/00* (2006.01)
  *G10L 17/06* (2013.01)
  *G16H 40/67* (2018.01)
  *G16H 50/70* (2018.01)
(52) U.S. Cl.
  CPC .......... *A61B 5/7278* (2013.01); *A61B 5/7282* (2013.01); *G16H 40/67* (2018.01); *G16H 50/70* (2018.01); *A61B 5/7246* (2013.01); *G10L 17/06* (2013.01)
(58) Field of Classification Search
  CPC .... A61B 5/7278; A61B 5/7282; G16H 40/67; G16H 50/70; G10L 17/06
  USPC .................................................. 600/529–543
  See application file for complete search history.

(56) References Cited

U.S. PATENT DOCUMENTS

| | | | |
|---|---|---|---|
| 2007/0073181 A1* | 3/2007 | Pu | A61B 5/0816 |
| | | | 600/529 |
| 2009/0312660 A1* | 12/2009 | Guarino | A61B 5/113 |
| | | | 600/529 |
| 2013/0144190 A1 | 6/2013 | Bruce | |
| 2013/0184601 A1 | 7/2013 | Zigel | |
| 2014/0350355 A1 | 11/2014 | Aisic | |
| 2015/0017367 A1 | 1/2015 | Sanderson | |
| 2015/0119741 A1* | 4/2015 | Zigel | A61B 5/7264 |
| | | | 600/529 |
| 2016/0270948 A1 | 9/2016 | Hariri | |
| 2016/0331303 A1 | 11/2016 | Shen | |
| 2017/0084295 A1 | 3/2017 | Tsiartas | |
| 2017/0270930 A1 | 9/2017 | Ozmeral | |
| 2019/0029563 A1* | 1/2019 | Sels | A61B 5/0002 |
| 2020/0093423 A1* | 3/2020 | Dafna | G16H 50/20 |

OTHER PUBLICATIONS

Singh Vishwanath Pratap et al: "IIIT-S CSSD: A Cough Speech Sounds Database", 2016 Twenty Second National Conference on Communication, IEEE, Mar. 4, 2016. pp. 1-6.
Pevernagie D. et al: "The Acoustics of Snoring", Sleep Medicine Reveiws, W. B. Suaunders, Amsterdam, NL, vol. 14, No. 2, Apr. 1, 2010, pp. 131-144.
M.J. Davey, "Epidemiological study of snoring from a random survey of 1075 participants." http://www.britishsnoring.co.uk/pdf/epidem.pdf, Nov. 28, 2016.
Lugaresi E., Cirignotta F., Coccoagna G. et al. (1980), "Some epidemiological data on snoring and cardiocirculatory disturbances". Sleep 3, 221-224.
Jose Maria Perez-Macias, Detection of Snores Using Source Separation on an Emfit Signal, IEEE Journa of Biomedical, 2018, 22 (4), 1157-1167.

* cited by examiner

DETECTING SUBJECTS WITH DISORDERED BREATHING

FIELD OF THE INVENTION

The disclosure relates to an apparatus and a method of operating the apparatus for detecting subjects with disordered breathing.

BACKGROUND OF THE INVENTION

Disordered breathing (e.g. sleep-disordered breathing) can be identified from the sounds that occur during respiration due to obstructions in the airway of a subject. Various types of obstructions are usually distinguishable in an anatomical or a physiological sense and can produce various types of sounds. A distinguishing feature of the sound caused by disordered breathing is its spectral signature. For example, palatal snoring is associated with a low frequency spectrum in the range from 100 Hz to 200 Hz, while stridor is associated with much higher frequencies.

In the case of heavy snoring, the snoring episodes can be easily identified from the intensity, energy or loudness pattern. Consequently, the snoring episodes can be separated from the other episodes and a common characterization of the snoring episodes can be made by any convenient frequency representation, such as Fourier transform (FT), power spectral density function (PSD), Mel-frequency cepstral coefficients (MFCC), or the transfer function of the synthesis filter of an estimated linear prediction (LP) system. US 2016/0331303 discloses an example method in which snoring is detected when it is determined that an audio signal includes characteristics of snoring.

However, a difficulty exists in the detection of disordered breathing according to existing techniques, since there is always a chance that there will be more than one person in an environment in which disordered breathing is detected. For example, it may be that multiple subjects are snoring simultaneously in the same environment. This results in inaccurate conclusions being drawn from sounds that are analyzed in such situations. Currently, there are no sound analysis systems that are capable of dealing with the presence of multiple subjects with disordered breathing. This means that systems are generally not used in the presence of multiple subjects or it is simply assumed that the findings (e.g. the total snoring time, the snoring sound level, or the snoring character, such as its spectral signature) derived by analyzing sounds from an environment are considerably inaccurate due to the potential that more than one subject with a breathing disorder is present in the environment.

The existing techniques typically use a level of the sound together with one or more features to detect disordered breathing. However, all of these features are compromised when there is more than one subject present with disordered breathing and there is currently no adequate way to resolve this. For example, where the sound level of an acoustic signal is used with the repetition rate of the acoustic signal to detect disordered breathing, the observation time (which is usually around several seconds) can be extended to a range where multiple repetitive frequencies can be resolved. However, the observation time would need to be extended such that it is of the order of minutes, which means that the repetitive patterns that are resolved are intrinsically hampered by drift. This can lead to a loss in accuracy of an identified repetition rate and thus an inaccuracy in the detection of disordered breathing. Similarly, if independent component analysis (ICA) is used to decompose the sound level, the required observation time for proper functioning of the analysis will conflict with the assumed stationarity of the sound level for a single subject with disordered breathing. Thus, there is no existing technique that provides the desired accuracy of results.

SUMMARY OF THE INVENTION

As noted above, a limitation with existing techniques for disordered breathing analysis is that the techniques are unable to produce accurate results where there exist multiple subjects with disordered breathing in the same environment. It would thus be valuable to address the limitations with existing techniques.

Therefore, according to a first aspect, there is provided an apparatus for detecting subjects with disordered breathing. The apparatus comprises one or more processors configured to acquire an acoustic signal from an acoustic sensor in an environment, determine a plurality of acoustic signal components from the acquired acoustic signal, determine a plurality of signal envelopes or energy signals based on the acoustic signal components, and analyze the determined plurality of signal envelopes or energy signals to detect whether there are one or more subjects in the environment with disordered breathing.

In some embodiments, the plurality of acoustic signal components may be for different features of acoustic signal components that distinguish the determined plurality of acoustic signal components from each other. In some embodiments, the plurality of acoustic signal components may be for any one or more of: different frequency ranges, different Mel-frequency cepstral coefficients, different acoustic levels, different temporal characters, and different spectral signatures.

In some embodiments, analyzing the determined plurality of signal envelopes or energy signals may comprise identifying repetition patterns in the determined plurality of signal envelopes or energy signals and a repetition interval for each of the identified repetition patterns.

In some embodiments, the one or more processors may be configured to compare the determined plurality of signal envelopes or energy signals, combine signal envelopes or energy signals that are similar, and identify the repetition patterns in the combined signal envelopes or energy signals.

In some embodiments, the one or more processors may be configured to analyze the determined plurality of signal envelopes or energy signals using independent component analysis, principal component analysis, multivariate singular spectrum analysis, or clustering algorithm analysis to determine a secondary plurality of signal envelopes or energy signals. In these embodiments, the one or more processors may be configured to identify the repetition patterns in the secondary determined plurality of signal envelopes or energy signals.

In some embodiments, the one or more processors may be configured to compare the identified repetition intervals and associated repetition patterns to reference data that is typical for disordered breathing to extract the identified repetition intervals and associated repetition patterns that relate to disordered breathing. In some embodiments, the reference data typical for disordered breathing may comprise breathing rate ranges typical for disordered breathing.

In some embodiments, the one or more processors may be configured to analyze the identified repetition intervals and associated repetition patterns to segment the acquired acoustic signal into parts and, for each part of the acquired acoustic signal, identify the number of substantially different breathing patterns in the part and assign a label to the part. In these embodiments, the label may be indicative of the identified number of substantially different breathing patterns in the part.

In some embodiments, the one or more processors may be configured to identify a part of the acquired acoustic signal corresponding to a disordered breathing episode for one subject and analyze at least one characteristic of the identified part of the acquired acoustic signal to identify the subject. In some embodiments, the one or more processors may be configured to analyze the at least one characteristic of the identified part of the acquired acoustic signal by matching the at least one characteristic of the identified part of the acquired acoustic signal to at least one corresponding characteristic stored in a memory with an identity of a subject to which the at least one corresponding characteristic relates and identifying the subject as the subject to which the at least one corresponding characteristic relates. In some embodiments, the one or more processors may be configured to analyze the identified part of the acquired acoustic signal to determine information on the disordered breathing of the identified subject.

In some embodiments, the disordered breathing may comprise any one or more of snoring, asthma, stridor, and apnea.

According to a second aspect, there is provided method of operating an apparatus for detecting subjects with disordered breathing. The method comprises acquiring an acoustic signal from an acoustic sensor in an environment, determining a plurality of acoustic signal components from the acquired acoustic signal, determining a plurality of signal envelopes or energy signals based on the acoustic signal components, and analyzing the determined plurality of signal envelopes or energy signals to detect whether there are one or more subjects in the environment with disordered breathing.

According to a third aspect, there is provided a computer program product comprising a computer readable medium, the computer readable medium having computer readable code embodied therein, and the computer readable code being configured such that, on execution by a suitable computer or processor, the computer or processor is caused to perform the method described above.

According to the aspects and embodiments described above, the limitations of existing techniques are addressed. In particular, the above-described aspects and embodiments enable the detection of whether there is one subject or more than one subject in an environment with disordered breathing. In this way, an assessment is made of the current situation, such that any subsequent processing can be adapted appropriately to account for there being one or more subjects in the environment with disordered breathing. This enables more accurate results to be provided. The limitations associated with the existing techniques discussed earlier are therefore addressed by way of the above-described aspects and embodiments.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

There is provided herein an apparatus and a method of operating the apparatus to detect subjects with disordered breathing. The term "disordered breathing" will be understood to encompass any form of breathing that is disordered. Generally, a subject exhibits disordered breathing when their airway is obstructed (or blocked). The airway of a subject may be obstructed in various ways. For example, the airway of a subject may be obstructed by the tongue of the subject blocking the airway, by a partial or complete upper airway occlusion (where the upper airway collapses), or any other type of obstruction, or any combination of obstructions. Examples of disordered breathing comprise any one or more of snoring, asthma, stridor, apnea, or any other type of disordered breathing, or any combination of types of disordered breathing. In some embodiments, the disordered breathing referred to herein may comprise sleep-disordered breathing (SDB), which is where a subject exhibits disordered breathing during sleep.

Figure 1:
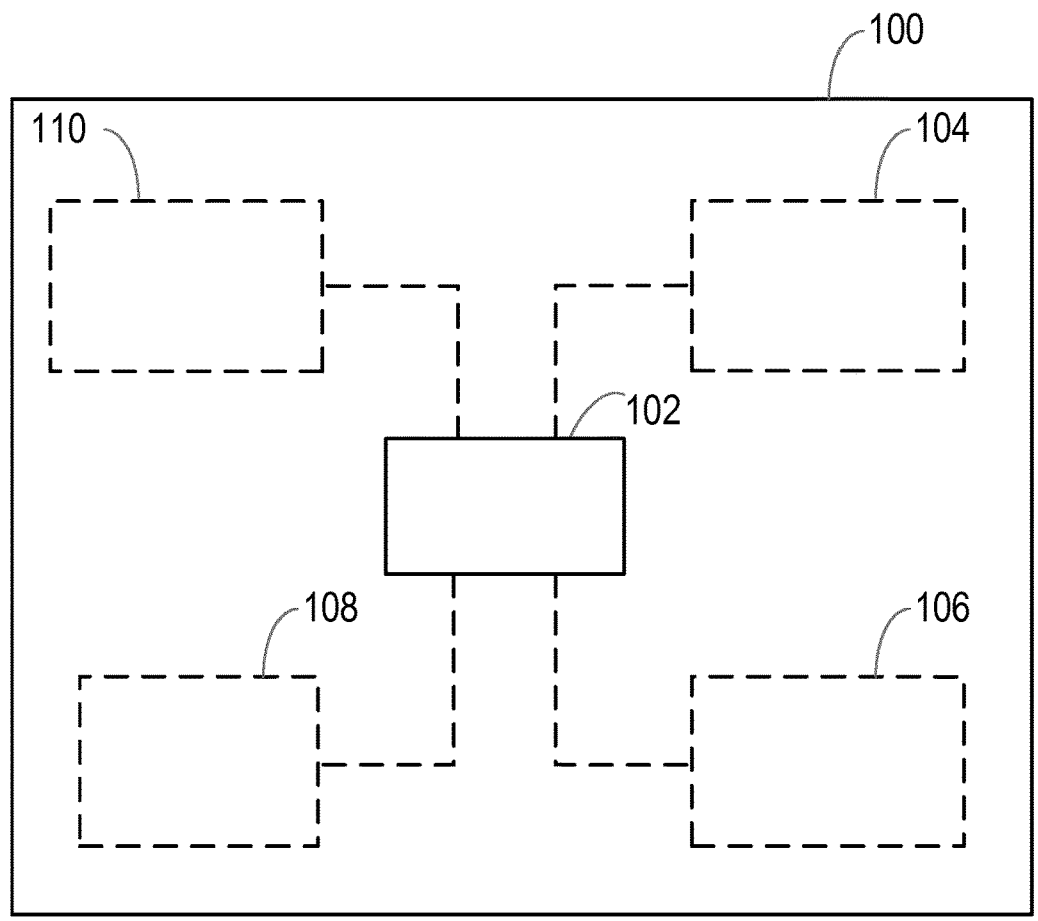
FIG. 1 is a block diagram of an apparatus according to an embodiment.

FIG. 1 illustrates a block diagram of an apparatus 100 for detecting subjects with disordered breathing according to an embodiment. As illustrated in FIG. 1, the apparatus 100 comprises one or more processors 102. Briefly, the one or more processors 102 are configured to acquire an acoustic (or audio) signal from an acoustic (or audio) sensor in an environment, determine a plurality of acoustic signal components from the acquired acoustic signal and determine a plurality of signal envelopes or energy signals based on the acoustic signal components. The one or more processors 102 are also configured to analyze the determined plurality of signal envelopes or energy signals to detect whether there are one or more subjects in the environment with disordered breathing.

It will be understood that a "signal envelope" referred to herein is an envelope of a signal. In more detail, a signal envelope can be a curve outlining the extremes of an oscillating signal. For example, a signal envelope can be a curve outlining the maxima of an oscillating signal and another signal envelope can be a curve outlining the minima of an oscillating signal. In this disclosure, the plurality of acoustic signal components are considered oscillating signals. Thus, herein, the plurality of signal envelopes are signal envelopes for the plurality of acoustic signal components.

It will also be understood that an "energy signal" referred to herein is a signal that is representative of the energy of an acoustic signal component for a certain portion of the acoustic signal component. The energy of an acoustic signal component for a certain portion of the acoustic signal component can be defined as the sum of the square of the amplitudes in that portion of the acoustic signal component. In some embodiments, the energy of an acoustic signal component for a certain portion of the acoustic signal component may be normalized by the length of the portion of the acoustic signal component.

The one or more processors 102 can be implemented in numerous ways, with software and/or hardware, to perform the various functions described herein. In some embodiments, each of the one or more processors 102 can be configured to perform individual or multiple steps of the method described herein. For example, in some embodiments, a single processor 102 may be configured to acquire the acoustic signal from the acoustic sensor in the environment, determine the plurality of acoustic signal components from the acquired acoustic signal, determine the plurality of signal envelopes or energy signals based on the acoustic signal components, and analyze the determined plurality of signal envelopes or energy signals to detect whether there are one or more subjects in the environment with disordered breathing. In other embodiments, one processor 102 may be configured to acquire the acoustic signal from the acoustic sensor in the environment, determine the plurality of acoustic signal components from the acquired acoustic signal and determine the plurality of signal envelopes or energy signals based on the acoustic signal components, and another processor 102 can be configured to analyze the determined plurality of signal envelopes or energy signals to detect whether there are one or more subjects in the environment with disordered breathing.

In particular implementations, the one or more processors 102 can comprise a plurality of software and/or hardware modules, each configured to perform, or that are for performing, individual or multiple steps of the method described herein. The one or more processors 102 may comprise one or more microprocessors, one or more multi-core processors and/or one or more digital signal processors (DSPs), one or more processing units, and/or one or more controllers (such as one or more microcontrollers) that may be configured or programmed (e.g. using software or computer program code) to perform the various functions described herein. The one or more processors 102 may be implemented as a combination of dedicated hardware (e.g. amplifiers, pre-amplifiers, analog-to-digital convertors (ADCs) and/or digital-to-analog convertors (DACs)) to perform some functions and one or more processors (e.g. one or more programmed microprocessors, DSPs and associated circuitry) to perform other functions.

As illustrated in FIG. 1, in some embodiments, the apparatus 100 may comprise a memory 104. Alternatively or in addition, the apparatus 100 (or, more specifically, the one or more processors 102) may be configured to communicate with and/or connect to a memory 104 external to (i.e. separate to or remote from) the apparatus 100. The memory 104 may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, the memory 104 can be configured to store program code that can be executed by the one or more processors 102 of the apparatus 100 to cause the one or more processors 102 to operate in the manner described herein.

Alternatively or in addition, in some embodiments, the memory 104 can be configured to store information resulting from or used in the method described herein. For example, in some embodiments, the memory 104 may be configured to store any one or more of the acoustic signal acquired from the acoustic sensor in the environment, the plurality of acoustic signal components determined from the acquired acoustic signal, the plurality of signal envelopes or energy signals determined based on the acoustic signal components, an indication of whether there are one or more subjects detected in the environment with disordered breathing, or any other information, or any combination of information, resulting from or used in the method described herein. The one or more processors 102 can be configured to control the memory 104 to store information resulting from or used in the method described herein.

As illustrated in FIG. 1, in some embodiments, the apparatus 100 may comprise a user interface 106. Alternatively or in addition, the apparatus 100 (or, more specifically, the one or more processors 102) may be configured to communicate with and/or connect to a user interface 106 external to (i.e. separate to or remote from) the apparatus 100. The user interface 106 can be configured to render (or output, display, or provide) information resulting from or used in the method described herein. For example, in some embodiments, the user interface 106 may be configured to render (or output, display, or provide) any one or more of the acoustic signal acquired from the acoustic sensor in the environment, the plurality of acoustic signal components determined from the acquired acoustic signal, the plurality of signal envelopes or energy signals determined based on the acoustic signal components, an indication of whether there are one or more subjects detected in the environment with disordered breathing, or any other information, or any combination of information, resulting from or used in the method described herein. The one or more processors 102 can be configured to control the user interface 106 to render information resulting from or used in the method described herein. Alternatively or in addition, the user interface 106 can be configured to receive a user input. For example, the user interface 106 may allow a user to manually enter information or instructions, interact with and/or control the apparatus 100.

Thus, the user interface 106 may be any user interface that enables the rendering (or outputting, displaying, or providing) of information and, alternatively or in addition, enables a user to provide a user input. For example, the user interface 106 may comprise one or more switches, one or more buttons, a keypad, a keyboard, a mouse, a touch screen or an application (e.g. on a smart device such as a tablet, a smartphone, or any other smart device), a display or display screen, a graphical user interface (GUI) such as a touch screen, or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces. In some embodiments, the user interface that is controlled to render information may be the same user interface as that which enables the user to provide a user input. The one or more processors 102 can be configured to control the user interface 106 to operate in the manner described herein.

As illustrated in FIG. 1, in some embodiments, the apparatus 100 may itself comprise the acoustic sensor 108 from which the acoustic signal is acquired. In these embodiments, the apparatus 100 comprising the acoustic sensor 108 may thus be in the environment. Alternatively or in addition, the apparatus 100 (or, more specifically, the one or more processors 102) may be configured to communicate with and/or connect to an acoustic sensor 108 external to (i.e. separate to or remote from) the apparatus 100. In some of these embodiments, an item (e.g. a standard mirror, a smart mirror, a light, such as a wake-up light, or any other item) or a device (e.g. a mobile device, a mobile phone, a smart phone, a tablet, or any other device) may comprise the acoustic sensor 108. Thus, the acoustic sensor 108 can, for example, be integrated in an item or a device in the environment according to some embodiments. In other embodiments, the acoustic sensor 108 may be a stand-alone acoustic sensor in the environment. For example, in some embodiments, the acoustic sensor 108 may be mounted on a surface, such as on a unit or wall, in the environment. The acoustic sensor 108 can be any sensor suitable to acquire an acoustic signal. Examples of an acoustic (or audio) sensor 108 include, but are not limited to, a microphone, an accelerometer, a laser Doppler vibrometer, a vibration pick-up sensor, or any other type of acoustic sensor, or any combination of acoustic sensors, suitable to acquire an acoustic (or audio) signal.

In some embodiments, the acoustic sensor 108 may itself comprise one or more processors 102. In these embodiments, the one or more processors 102 of the acoustic sensor 108 can be configured to acquire the acoustic signal from the acoustic sensor 108, determine the plurality of acoustic signal components from the acquired acoustic signal and determine the plurality of signal envelopes or energy signals based on the acoustic signal components. In some of these embodiments, the one or more processors 102 of the acoustic sensor 108 can then be configured to transmit the determined plurality of signal envelopes or energy signals to one or more processors 102 of the apparatus 100 for analysis in the manner described herein.

As illustrated in FIG. 1, in some embodiments, the apparatus 100 may comprise a communications interface (or communications circuitry) 110. The communications interface 110 can be for enabling the apparatus 100 (or any components of the apparatus 100, such as the one or more processors 102, the memory 104, the user interface 106, the acoustic sensor 108, and/or any other components of the apparatus 100) to communicate with and/or connect to one or more other components, such as other sensors, interfaces, devices, memories, etc. The communications interface 110 may enable the apparatus 100 (or any components of the apparatus 100) to communicate and/or connect in any suitable way. For example, the communications interface 110 may enable the apparatus 100 (or any components of the apparatus 100) to communicate and/or connect wirelessly, via a wired connection, or via any other communication (or data transfer) mechanism. In some wireless embodiments, for example, the communications interface 110 may enable the apparatus 100 (or any components of the apparatus 100) to use radio frequency (RF), Bluetooth, or any other wireless communication technology to communicate and/or connect.

Although not illustrated in FIG. 1, the apparatus 100 may comprise a battery or other power supply for powering the apparatus 100 or means for connecting the apparatus 100 to a mains power supply. It will also be understood that the apparatus 100 may comprise any other component to those described herein or any combination of components.

Figure 2:
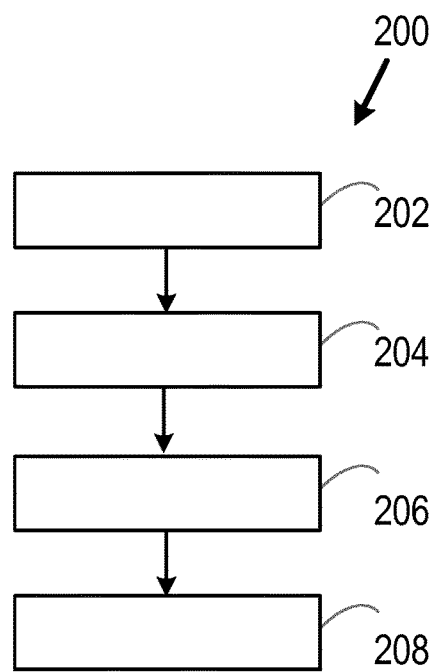
FIG. 2 is a block diagram of a method according to an embodiment.
Figure 3:
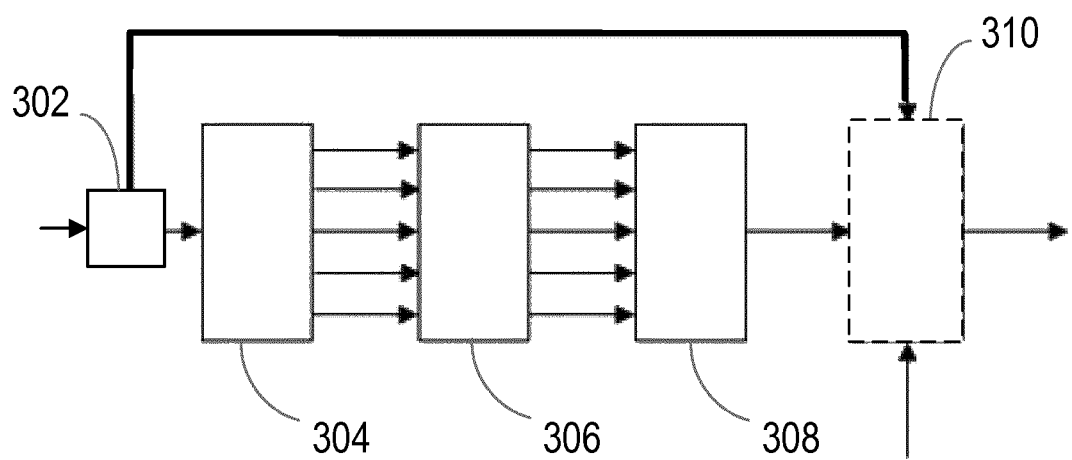
FIG. 3 is a block diagram of a method according to another embodiment.

FIG. 2 illustrates a method 200 of operating an apparatus 100 (as described earlier with reference to FIG. 1) to detect subjects with disordered breathing according to an embodiment. As described earlier, the apparatus 100 comprises one or more processor 102. The method 200 illustrated in FIG. 2 can generally be performed by or under the control of the one or more processors 102. FIG. 3 illustrates in more detail the method performed by the one or more processors 102 according to an embodiment.

With reference to FIGS. 2 and 3, at block 202 of FIG. 2 and block 302 of FIG. 3, an acoustic (or audio) signal is acquired from an acoustic (or audio) sensor 108 in an environment. More specifically, the acoustic signal is acquired by the one or more processors 102 from the acoustic sensor 108 in the environment. As mentioned earlier, the acoustic sensor 108 can be an acoustic sensor of the apparatus 100 itself or an acoustic sensor that is external to (i.e. separate to or remote from) the apparatus 100.

At block 204 of FIG. 2 and block 304 of FIG. 3, a plurality of acoustic signal components are determined from the acquired acoustic signal. More specifically, the plurality of acoustic signal components are determined from the acquired acoustic signal by the one or more processors 102. Thus, in effect, the acquired acoustic signal can be split into multiple acoustic signal components. In some embodiments, the plurality of acoustic signal components that are determined from the acquired acoustic signal may be downsampled at block 204 of FIG. 2 and block 304 of FIG. 3. In this way, the computational complexity of the subsequent method can be reduced, which can conserve computational resources and power.

In some embodiments, the plurality of acoustic signal components that are determined at block 204 of FIG. 2 and block 304 of FIG. 3 may be associated with different features of acoustic signal components that distinguish the determined plurality of acoustic signal components from each other. For example, the plurality of acoustic signal components can be for any one or more of different frequency ranges (or different frequency bands), different Mel-frequency cepstral coefficients (MFCCs), different acoustic levels (or different sound levels), different temporal characters (e.g. different breathing rates), different spectral signatures (e.g. different dominant frequency ranges), or any other feature, or any combination of features, that distinguish the determined plurality of acoustic signal components from each other. Although examples have been provided for the different features of acoustic signal components that can distinguish the determined plurality of acoustic signal components from each other, it will be understood that the plurality of acoustic signal components may be associated with any other feature, or any combination of features, suitable to distinguish those acoustic signal components from each other and a person skilled in the art will be aware of such other features that may be used.

In an example, the plurality of acoustic signal components are associated with different frequency ranges. For example, each of the acoustic signal components may be indicative of a different (or certain) frequency range. In some embodiments, the one or more processors 102 may be configured to determine the plurality of acoustic signal components from the acquired acoustic signal using a band splitter. Examples of a band splitter that may be used include, but are not limited to, an octave band splitter, or any other suitable band splitter. In some embodiments, the one or more processors 102 may implement an adaptive method for frequency range selection or a data-driven method to determine the plurality of acoustic signal components from the acquired acoustic signal. Examples of data-driven methods that may be used include, but are not limited to, singular spectrum analysis (SSA), empirical mode decomposition (EMD), or any other suitable data-driven method.

At block 206 of FIG. 2 and block 306 of FIG. 3, a plurality of signal envelopes or energy signals are determined based on the acoustic signal components. More specifically, a plurality of signal envelopes or energy signals are determined by the one or more processors 102 based on the acoustic signal components. Thus, a plurality of signal envelopes or energy signals are created from the acoustic signal components. In effect, the combination of blocks 204 and 206 of FIG. 2 (and, similarly, blocks 304 and 306 of FIG. 3) create multiple signals from a single acquired acoustic signal. More specifically, multiple signal envelopes or energy signals are created. These multiple signals that are created can be considered as acoustic features of the acquired acoustic signal. A person skilled in the art will be aware of various techniques that can be used to determine a plurality of signal envelopes or energy signals based on acoustic signal components. For example, in some embodiments, the one or more processors 102 may be configured to determine the plurality of signal envelopes or energy signals based on the acoustic signal components by using, for each acoustic signal component, a squaring operation on the signal values, followed by an averaging operation and a non-linear mapping (e.g. a logarithmic mapping or a decibel mapping). In some embodiments, the plurality of signal envelopes or energy signals that are determined based on the acoustic signal components may be down-sampled at block 206 of FIG. 2 and block 306 of FIG. 3. In this way, the computational complexity of the subsequent method can be reduced, which can conserve computational resources and power.

At block 208 of FIG. 2 and block 308 of FIG. 3, the determined plurality of signal envelopes or energy signals are analyzed to detect whether there are one or more subjects in the environment with disordered breathing. More specifically, the determined plurality of signal envelopes or energy signals are analyzed by the one or more processors 102 to detect whether there are one or more subjects in the environment with disordered breathing. In some embodiments, analyzing the determined plurality of signal envelopes or energy signals may comprise identifying any co-occurrences of events (or simultaneous events) in the signal envelopes or energy signals. Such simultaneous events may for instance be simultaneous increases and/or decreases in a subset of the plurality of signal envelopes or energy signals. In some embodiments, analyzing the determined plurality of signal envelopes or energy signals may comprise identifying repetition patterns in the determined plurality of signal envelopes or energy signals. More specifically, the one or more processors 102 may be configured to identify repetition patterns in the determined plurality of signal envelopes or energy signals according to some embodiments. For example, analyzing the determined plurality of signal envelopes or energy signals can comprise identifying any co-occurrences of events (or simultaneous events) in the signal envelopes or energy signals and identifying repetition patterns of these events according to some embodiments. The number of repetitive patterns that are identified can be indicative of the number of different subjects in the environment with disordered breathing. In some embodiments, the one or more processors 102 may be configured to determine an autocorrelation function (ACF) for the signal envelopes or energy signals to identify the repetition patterns in the signal envelopes or energy signals.

In more detail, for example, the one or more processors 102 can be configured to determine an autocorrelation function (ACF) of each of the plurality of signal envelopes or energy signals. From each of the autocorrelation functions (ACFs) that are determined, the one or more processors 102 may be configured to check if there are indications for repetition in the signal envelope or energy signal. In this way, the one or more processors 102 can be configured to identify repetition patterns in the plurality of signal envelopes or energy signals. The one or more processors 102 may be configured to compare the plurality of signal envelopes or energy signals to each other. Where the plurality of signal envelopes or energy signals are determined based on acoustic signal components associated with different frequency ranges, the comparison of the plurality of signal envelopes or energy signals to each other can thus be a comparison of signal envelopes or energy signals associated with the different frequency ranges. The one or more processors 102 may implement a decision engine (e.g. incorporating heuristic rules) to determine if the identified repetition patterns are indicative of one or more (e.g. essentially) different signal envelopes or energy signals.

According to other embodiments, the one or more processors 102 may be configured to compare the determined plurality of signal envelopes or energy signals and combine (e.g. merge) signal envelopes or energy signals that are similar. A signal envelope or energy signal may be similar to another signal envelope or energy signal where those signal envelopes or energy signals differ by less than a predefined degree or value, or have more than a predefined number of characteristics in common. In embodiments where similar signal envelopes or energy signals are combined, the one or more processors 102 can be configured to identify the repetition patterns in the combined signal envelopes or energy signals. In some of these embodiments, the one or more processors 102 may be configured to determine an autocorrelation function (ACF) for the combined signal envelopes or energy signals to identify the repetition patterns in the combined signal envelopes or energy signals.

In more detail, for example, the one or more processors 102 may be configured to compare the plurality of signal envelopes or energy signals to each other. Based on the comparison, the one or more processors 102 can be configured to determine whether the plurality of signal envelopes or energy signals are (e.g. essentially) different signal envelopes or energy signals. The one or more processors 102 can be configured to combine (e.g. merge) signal envelopes or energy signals that are similar. For example, the signal envelopes or energy signals with similar patterns can be combined. In this example, the one or more processors 102 can be configured to determine an autocorrelation function (ACF) of the combined signal envelopes or energy signals. The one or more processors 102 may be configured to check the autocorrelation function (ACF) of the combined signal envelopes or energy signals for repetitive patterns. In this way, the one or more processors 102 can be configured to identify repetition patterns in the plurality of signal envelopes or energy signals. The one or more processors 102 may implement a decision engine (e.g. incorporating heuristic rules) to determine if the identified repetition patterns are indicative of one or more (e.g. essentially) different signal envelopes or energy signals.

According to other embodiments, the one or more processors 102 may be configured to analyze the determined plurality of signal envelopes or energy signals using independent component analysis (ICA), principal component analysis (PCA), multivariate singular spectrum analysis (MSSA), or clustering algorithm analysis to determine a secondary plurality of signal envelopes or energy signals. In these embodiments, the one or more processors 102 can be configured to identify the repetition patterns in the secondary determined plurality of signal envelopes or energy signals. In some of these embodiments, the one or more processors 102 may be configured to determine an autocorrelation function (ACF) for the secondary determined plurality of signal envelopes or energy signals to identify the repetition patterns in the secondary determined plurality of signal envelopes or energy signals.

In more detail, for example, the one or more processors 102 may be configured to input the plurality of signal envelopes or energy signals into an algorithm to find underlying structures. For example, the plurality of signal envelopes or energy signals may be analyzed using independent component analysis (ICA), principal component analysis (PCA), multivariate singular spectrum analysis (MSSA), or clustering algorithms to determine a secondary plurality of signal envelopes or energy signals. The one or more processors 102 may be configured to input the secondary plurality of signal envelopes or energy signals into an autocorrelation function (ACF) mechanism. In this way, the one or more processors 102 can be configured to determine an autocorrelation function (ACF) for the secondary determined plurality of signal envelopes or energy signals to identify the repetition patterns in the secondary determined plurality of signal envelopes or energy signals. The one or more processors 102 may implement a decision engine (e.g. incorporating heuristic rules) to determine if the identified repetition patterns are indicative of one or more (e.g. essentially) different signal envelopes or energy signals.

In any of the embodiments described herein where repetition patterns are identified, the one or more processors 102 may optionally further be configured to identify a repetition interval for each of the identified repetition patterns. For example, the one or more processors 102 may be configured to determine the fundamental interval of repetition for the identified repetition patterns. In embodiments where an autocorrelation function (ACF) is determined, the repetition interval for an identified repetition pattern can be identified from a peak in the autocorrelation function (ACF) according to some embodiments. Although an autocorrelation function (ACF) has been provided herein as an example of the function that may be determined to identify repetition patterns, it will be understood that any other types of function (e.g. transformation) may be used to identify repetition patterns and a person skilled in the art will be aware of other types of function that may be used.

Returning again to FIG. 3, in some embodiments where repetition intervals are identified for the identified repetition patterns, at block 310 of FIG. 3, the one or more processors 102 may be configured to compare the identified repetition intervals and the associated repetition patterns to reference data to extract the identified repetition intervals and associated repetition patterns that relate to disordered breathing. In this way, the identified repetition intervals and the associated repetition patterns can be validated. More specifically, by extracting the identified repetition intervals and the associated repetition patterns that relate to disordered breathing in the manner described, it is possible to eliminate spurious (e.g. accidentally found) and/or insignificant repetition patterns and their associated repetition intervals. Thus, more relevant ones of the identified repetition intervals and associated repetition patterns are extracted. In some embodiments, the one or more processors 102 may input the identified repetition intervals and the associated repetition patterns into a validation unit for the comparison of the identified repetition intervals and the associated repetition patterns to reference data.

In some embodiments, the reference data used for the comparison can be reference data that is typical for disordered breathing according to some embodiments. For example, the reference data may comprise breathing rate ranges typical for disordered breathing or any other type of ranges typical for disordered breathing. The ranges typical for disordered breathing may be ranges that are personalized to one or more subjects according to some embodiments. The reference data may comprise data that is acquired based on a priori knowledge and/or based on its relevance to the identified repetition intervals and the associated repetition patterns.

In some embodiments, the reference data used for the comparison can comprise the original acoustic signal acquired from the acoustic sensor 108. For example, in some embodiments, the one or more processors 102 may be configured to create a reference signal envelope or energy signal from the (e.g. full band) acoustic signal acquired from the acoustic sensor 108 or from an excitation signal obtained by filtering the acoustic signal acquired from the acoustic sensor. Examples of such filtering that may be used to filter the acoustic signal include, but are not limited to, low-pass filtering, linear prediction analysis filtering, or similar. The one or more processors 102 may then be configured to decompose the created reference signal envelope or energy signal into the identified repetitive patterns. The one or more processors 102 can be configured to check whether the identified repetitive patterns are in fact significant patterns in the created reference signal envelope or energy signal. For example, the one or more processors 102 may use coefficients of the decomposition as determinants for the relative importance of the identified repetitive patterns in the created reference signal envelope or energy signal. Thus, repetitive patterns that are negligible compared to others can be eliminated.

As mentioned earlier, the number of repetitive patterns that are identified can be indicative of the number of different subjects in the environment with disordered breathing. Thus, in embodiments where the identified repetition intervals and associated repetition patterns that relate to disordered breathing are extracted, the number of repetitive patterns that are identified and hence the number of different subjects in the environment with disordered breathing can be validated. The output of the one or more processors 102 according to some embodiments (e.g. the output at block 310 of FIG. 3) can be the number of subjects with disordered breathing or the validated number of subjects with disordered breathing. Alternatively or in addition, in some embodiments, the output of the one or more processors 102 (e.g. the output at block 310 of FIG. 3) can be one or more of the determined plurality of signal envelopes or energy signals and/or the identified repetition patterns for one or more of the determined plurality of signal envelopes or energy signals.

Although not illustrated in FIG. 2 or 3, in some embodiments, the one or more processors 102 may be further configured to analyze the identified repetition intervals and the associated repetition patterns to segment the acquired acoustic signal into parts. In some of these embodiments, for each part of the acquired acoustic signal, the one or more processors 102 may also be configured to identify the number of different (or substantially different) breathing patterns in the part. This number can be indicative of the number of different subjects in the environment with disordered breathing. According to some embodiments, for each part of the acquired acoustic signal, the one or more processors 102 may be configured to assign a label (e.g. metadata) to the part. In some embodiments, the label may be indicative of the identified number of different (or substantially different) breathing patterns in the part. For example, the label may be indicative that there are zero, one, or multiple different (or substantially different) breathing patterns in the part.

In some embodiments where the acquired acoustic signal is segmented into parts, the one or more processors 102 may be configured to identify a part of the acquired acoustic signal corresponding to a disordered breathing episode (or epoch) for one subject. Thus, a part of the acquired acoustic signal corresponding to a disordered breathing episode for a single subject can be identified. In some of these embodiments, the one or more processors 102 may be further configured to analyze the identified part of the acquired acoustic signal to determine information on the disordered breathing of the subject. The information on the disordered breathing of the subject can, for example, comprise any one or more of a duration of the disordered breathing of the subject, an intensity of the disordered breathing of the subject, a score for the disordered breathing of the subject, or any other information, or any combination of information, on the disordered breathing of the subject. In some embodiments, the one or more processors 102 can be configured to apply a label (e.g. metadata) to the identified part of the acquired acoustic signal to indicate that it relates to a single subject and/or to indicate the determined information on the disordered breathing of the subject.

In some embodiments where a part of the acquired acoustic signal corresponding to a disordered breathing episode for one subject is identified, the one or more processors 102 may also be configured to analyze at least one characteristic of the identified part of the acquired acoustic signal to identify the subject. For example, in some embodiments, the one or more processors 102 can be configured to analyze the at least one characteristic of the identified part of the acquired acoustic signal by matching the at least one characteristic of the identified part of the acquired acoustic signal to at least one corresponding characteristic stored in a memory 104 with an identity of a subject to which the at least one corresponding characteristic relates and identifying the subject as the subject to which the at least one corresponding characteristic relates. The at least one characteristic can be any one or more characteristics that are specific to a particular subject. Examples of the at least one characteristic include, but are not limited to, any one or more of a breathing rate, a breathing intensity, a spectral signature, or any other characteristic, or any combination of characteristics specific to a particular subject.

Alternatively or in addition, in some embodiments, the one or more processors 102 can be configured to identify the subject by outputting a request for a user of the apparatus 100 to identify the subject via a user interface 106. In these embodiments, the identity of the subject may then be received at the user interface 106. In some embodiments, the one or more processors 102 can be configured to identify the subject by outputting a request for a user of the apparatus 100 to identify the subject via a user interface 106 until the one or more processors 102 has knowledge of the at least one characteristic that is specific to the subject. The one or more processors 102 can be configured to store the at least one characteristic in the memory 104, once known, such that the at least one characteristic can subsequently be used in the manner described earlier to identify the subject. In this way, future requests to the user for labelling become unnecessary.

In some embodiments where a subject is identified, the one or more processors 102 may also be configured to analyze the identified part of the acquired acoustic signal to determine information on the disordered breathing of the identified subject. The information on the disordered breathing of the identified subject can, for example, comprise any one or more of a duration of the disordered breathing of the identified subject, an intensity of the disordered breathing of the identified subject, a score for the disordered breathing of the identified subject, or any other information, or any combination of information, on the disordered breathing of the identified subject. In some embodiments, the one or more processors 102 can be configured to apply a label (e.g. metadata) to the identified part of the acquired acoustic signal to indicate that it relates to the identified subject (e.g. the identity of the subject may be provided in the applied label) and/or to indicate the determined information on the disordered breathing of the identified subject.

According to an embodiment, for example, the one or more processors 102 may be configured to segment the acquired acoustic signal into parts by analyzing (or interpreting) the identified repetition intervals and the associated repetition patterns to subdivide a time axis of a whole night (e.g. from a start to an end of a sound measurement) into parts. These parts can be labelled as 0, 1 or 2 to indicate the number of subjects in the parts with disordered breathing. Alternatively or additionally, the acquired acoustic signal can be subdivided into intervals where, in a case of two subjects A and B with disordered breathing, no disordered breathing is detected, the disordered breathing of subject A is detected, the disordered breathing of subject B is detected, or the disordered breathing of subject of both subjects A and B are detected. This subdivision allows a relevant overview of disordered breathing in the night to be acquired for each of the subjects with disordered breathing from the pertinent intervals.

For example, the one or more processor 102 may identify a part of the acquired acoustic signal labelled as 1, which corresponds to a disordered breathing episode for one subject. The one or more processors 102 can be configured to analyze one particular part labelled 1 for one or more characteristics that may identify the subject and the variability in said part. This data can then be used as a reference for comparison with data of all other parts labelled as 1, where a similarity metric can be derived from the variability. The parts labelled as 1 may be subdivided into two sets: one identical to the reference and the other not identical to the reference according to the similarity metric. The sets may be labelled as 1A and 1B, respectively. In case of sufficient parts identified as 1, a clustering method may be applied to split the set of parts labelled as one into two sets.

The one or more processors 102 can be configured to analyze the identified part labelled as 1A and 1B to determine information on the disordered breathing of the identified subjects. For example, the overall duration of disordered breathing of subject A can be determined as the sum of the parts labelled 1A and 2 and the overall duration of disordered breathing of subject B can be determined as the sum of the parts labelled 1B and 2. The one or more characteristics of subjects 1A and 1B can be acquired, for example, from a spectral analysis of the parts labelled as 1A or 1B. In the simplest form, it may be assumed that parts labelled as 2 are an extrapolation of the measurements of both subjects 1A and 1B.

Figure 4:
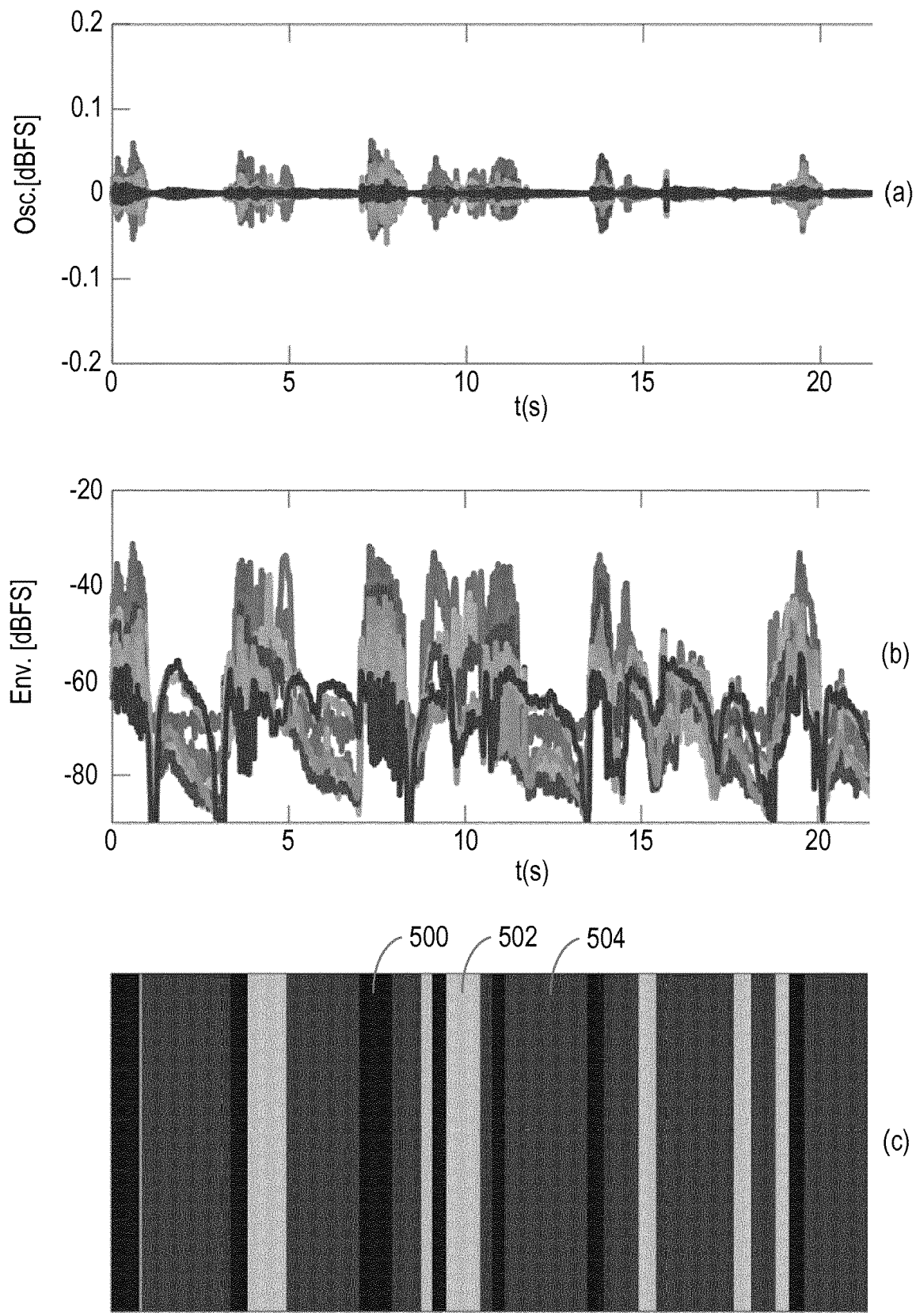
FIG. 4 is an illustration of example signals according to an embodiment.

FIG. 4 illustrates some example signals according to an embodiment. In more detail, FIG. 4(a) illustrates an acquired acoustic signal over time, which is split into a plurality of different acoustic signal components (which are shown by the different shades of grey). The plurality of different acoustic signal components are determined from the acquired acoustic signal in the manner described herein. The vertical axis of FIG. 4(a) represents the oscillations of the acquired acoustic signal in decibels relative to full scale dBFS (where full scale equals 1). The horizontal axis of FIG. 4(a) represents time in seconds. In FIG. 4(a), the plurality of different acoustic signal components are thus illustrated over time. As mentioned earlier, the plurality of acoustic signal components are considered oscillating signals. In the illustrated example embodiment of FIG. 4(a), the plurality of different acoustic signal components are for different frequency ranges (or different frequency bands). For example, the acquired acoustic signal may be filtered into different frequency ranges to determine the plurality of different acoustic signal components that are illustrated in FIG. 4(a).

FIG. 4(b) illustrates a plurality of signal envelopes (which are shown by the different shades of grey) determined based on the acoustic signal components of FIG. 4(a) in the manner described herein. More specifically, in the illustrated example embodiment of FIG. 4(b), the plurality of signal envelopes are for the different frequency ranges. The vertical axis of FIG. 4(b) represents the envelopes of the acoustic signal components in decibels relative to full scale dBFS (where full scale equals 1). The horizontal axis of FIG. 4(b) represents time in seconds. In FIG. 4(b), the plurality of signal envelopes are thus illustrated over time. The plurality of signal envelopes of FIG. 4(b) are analyzed in the manner described herein to detect whether there are one or more subjects in the environment with disordered breathing. FIG. 4(c) illustrates an output of this detection.

As illustrated in FIG. 4(c), it is detected that there are two subjects with disordered breathing in the environment according to this illustrated example embodiment. The output illustrated in FIG. 4(c) identifies times at which disordered breathing of a first subject is detected in the environment (which are illustrated by the grey shade labelled as 500), times at which disordered breathing of a second subject is detected in the environment (which are illustrated by the grey shade labelled as 502), and times at which no disordered breathing is detected or the disordered breathing of the first subject and the second subject is detected simultaneously (which are illustrated by the grey shade labelled as 504).

Figure 5:
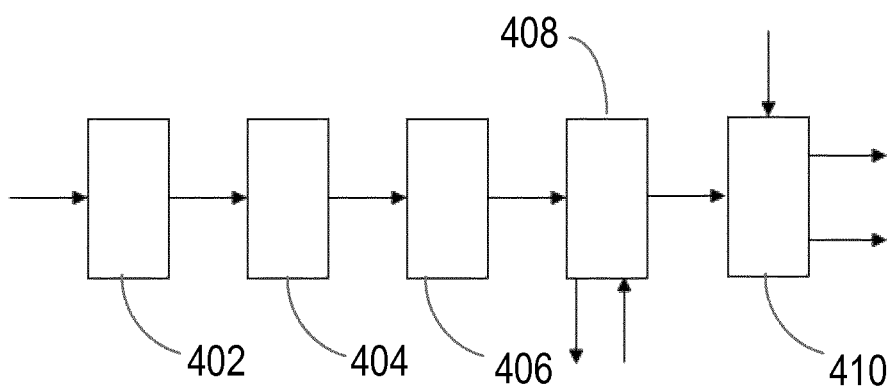
FIG. 5 is a block diagram of a method according to another embodiment.

FIG. 5 illustrates a method related to labelling parts of the acquired acoustic signal corresponding to a disordered breathing episode for a subject according to an embodiment. The method can be performed by or under the control of the one or more processors 102. The input to block 402 of FIG. 5 is one or more identified parts of the acquired acoustic signal corresponding to a disordered breathing episode for the one subject. At block 402 of FIG. 5, the one or more identified parts of the acquired acoustic signal are analyzed to generate a set of features for each identified part of the acquired acoustic signal.

At block 404 of FIG. 5, the one or more processors 102 can be configured to cluster the one or more identified parts into at least two clusters based on the set of features generated for the one or more identified parts. In this way, the interaction with the user can be reduced. For example, identified parts with the same or similar set of features may form a cluster. In some embodiments, at block 404 of FIG. 5, the one or more processors 102 can be configured to receive an input from a memory 104 containing information on labelling for the at least two clusters, which is stored in the memory 104 based on past labelling. In this way, where possible, the identified parts of the acoustic signal can be assigned a label based on past labelling. At block 406 of FIG. 5, the one or more processors 102 can be configured to identify at least one characteristic (e.g. a representative event) of each cluster that is representative of the cluster.

At block 408 of FIG. 5, the one or more processors 102 can be configured to output a request for a label (e.g. metadata), as illustrated by way of the downward arrow from block 408 of FIG. 5. Thus, in effect, the one or more processors 102 can be configured to signal the need for a label (e.g. metadata) to a user of the apparatus 100 to identify the subject. For example, the one or more processors 102 may be configured to playback at least one identified characteristic for a cluster to the user with a request for the user to provide a label (e.g. metadata) that identifies the subject from which the at least one characteristic originates. In some embodiments, the one or more processors 102 can be configured to control a messaging unit to output the request for the label. Also, at block 408 of FIG. 5, the label can be received by the one or more processors 102 in response to the request via a user interface 106, as illustrated by way of the upward arrow to block 408 of FIG. 5. Thus, the clusters can be provided with labels. In some embodiments, the one or more processors 102 can be configured to label all clusters (or, more specifically, all parts of the acquired acoustic signal) in this way. In some embodiments, block 408 of FIG. 5 may only be performed where there are parts of the acoustic signal without labels or with unclear (or ambiguous) labels assigned based on past labelling.

At block 410 of FIG. 5, the one or more processors 102 may be configured to create individual overviews for each identified subject with the received labels. As illustrated by the arrows to the right of box 410 of FIG. 5, the one or more processors 102 can also be configured to output the created individual overviews for each identified subject. In particular, at block 410 of FIG. 5, the one or more processors 102 can be configured to receive the acquired acoustic signal and/or label (e.g. metadata), as illustrated by the downward arrow to block 410 of FIG. 5, from which the overviews for each identified subject can be created. In some embodiments, the overviews may comprise information determined on the disordered breathing of the identified subject, such as a total duration that the identified subject exhibited disordered breathing during a predefined time period (e.g. during the night), an average level of disordered breathing for the identified subject, a spectral character for the identified subject, or any other information, or any combination of information, determined on the disordered breathing of the identified subject.

In some embodiments, the analysis of the determined plurality of signal envelopes or energy signals described earlier can be extended to a more refined analysis. For example, more insight into (e.g. parts of) breathing cycles of subjects may be gained where the one or more processors 102 are configured to divide a time axis for the signal envelopes or energy signals into a more detailed description. The one or more processors 102 may also be configured with options to differentiate between an inhale phase and an exhale phase of one or more subjects. This may, for example, be an extension of the validation unit mentioned earlier. In some of these embodiments, the one or more processors 102 can be configured to output the determined number of subjects with disordered breathing and whether a subject with disordered breathing is further characterized with inhale and exhale phases.

In some embodiments, the method described herein may also be performed in respect of at least one other acoustic (or audio) signal acquired from at least one other acoustic (or audio) sensor 108 in the environment. Thus, the method described herein can be performed in respect of acoustic signals acquired from at least two different acoustic sensors 108 in the environment according to some embodiments. Thus, the method can be seamlessly extended to multiple sensor systems. In some embodiments, the at least two acoustic sensors 108 may be placed at different locations in the environment. In this way, at least one other plurality of signal envelopes or energy signals can be determined. In effect, according to these embodiments, more than one set of signal envelopes or energy signals are determined. Thus, more than one set of signal envelopes or energy signals may be analyzed in the manner described herein according to some embodiments. In some embodiments where more than one set of signal envelopes or energy signals is determined, the sets of signal envelopes or energy signals may be merged into a single set for analysis in the manner described herein.

In some embodiments, the acoustic signal may be acquired by one or more processors 102 of the acoustic sensor 108, the plurality of acoustic signal components may be determined by the one or more processor 102 of the acoustic sensor 108 and the plurality of signal envelopes or energy signals may be determined by the one or more processors 102 of the acoustic sensor 108. In some of these embodiments, where the method described earlier is also performed in respect of at least one other acoustic signal acquired from at least one other acoustic sensor 108 in the environment, the signal envelopes or energy signals determined by the one or more processors 102 of the acoustic sensors 108 may be transmitted from one acoustic sensor 108 to another. In some embodiments, the acoustic sensor 108 that receives a signal envelope or energy signal from another acoustic sensor 108 can be configured to synchronize the received signal envelope or energy signal with its own signal envelope or energy signal. In this way, one or more processors 102 can acquire synchronized signal envelopes or energy signals and analyze these synchronized signal envelopes or energy signals in the manner described herein. Alternatively, in some embodiments, one or more processors 102 may acquire the unsynchronized signal envelope or energy signal from the acoustic sensors 108 and the one or more processors 102 can be configured to synchronize the acquired acoustic signals.

In some embodiments, the at least one other plurality of signal envelopes or energy signals can be determined in a similar manner to the previously described plurality of signal envelopes or energy signals. More specifically, according to some embodiments, the plurality of acoustic signal components that are determined from the at least one other acquired acoustic signal may be associated with the same type of features as the previously described plurality of acoustic signal components. For example, where the plurality of acoustic signal components determined from the previously described acoustic signal are associated with different frequency ranges, the plurality of acoustic signal components determined from the at least one other acquired acoustic signal may also be associated with different frequency ranges.

In any of the embodiments described herein, at least one or all of the steps that the one or more processors 102 are configured to perform can be automated.

There is also provided a computer program product comprising a computer readable medium. The computer readable medium has computer readable code embodied therein. The computer readable code is configured such that, on execution by a suitable computer or processor (such as the one or more processors 102 of the apparatus 100 or any other processor), the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an apparatus, a method and a computer program product that address the limitations associated with the existing techniques.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A sound analysis apparatus for detecting a presence of multiple subjects in an environment with sleep disordered breathing, the apparatus comprising:

an acoustic sensor configured to acquire an acoustic signal in the environment;

one or more processors configured to:

determine a plurality of acoustic signal components from the acquired acoustic signal, the plurality of acoustic signal components differing from one another in respect of at least one signal characteristic or property;

determine a plurality of signal envelopes or energy signals based on the acoustic signal components, at least one signal envelope being derived from each of the acoustic signal components of the plurality of acoustic signal components; and analyze the determined plurality of signal envelopes or energy signals to detect whether there are one or more subjects in the environment with sleep disordered breathing, wherein analyzing comprises identifying (i) a number of repetition patterns in the determined plurality of signal envelopes or energy signals and (ii) a repetition interval for each of the identified repetition patterns, and further analyzing the number of repetition patterns and the repetition intervals to subdivide a time axis of a whole duration from a start to an end of a sound measurement of the acquired acoustic signal and provide an overview of sleep disordered breathing to be acquired for each subject, wherein the number of repetition patterns identified in each subdivided interval is indicative of a number of different subjects in the environment with sleep disordered breathing; and a user interface configured to render information relating to sleep disordered breathing based on the detected one or more subjects in the environment with sleep disordered breathing, wherein the rendered information includes an identification of the detected one or more subjects and one or more characteristic of the detected sleep disordered breathing of a respective detected and identified subject.

2. An apparatus as claimed in claim 1, wherein the plurality of acoustic signal components is for any one or more of:
different frequency ranges;
different Mel-frequency cepstral coefficients;
different acoustic levels;
different temporal characters; and
different spectral signatures.

3. An apparatus as claimed in claim 1, wherein the one or more processors are configured to:
compare the determined plurality of signal envelopes or energy signals;
combine signal envelopes or energy signals that are similar; and
identify the repetition patterns in the combined signal envelopes or energy signals.

4. An apparatus as claimed in claim 1, wherein the one or more processors are configured to:
analyze the determined plurality of signal envelopes or energy signals using independent component analysis, principal component analysis, multivariate singular spectrum analysis, or clustering algorithm analysis to determine a secondary plurality of signal envelopes or energy signals; and
identify the repetition patterns in the secondary determined plurality of signal envelopes or energy signals.

5. An apparatus as claimed in claim 1, wherein the one or more processors are configured to:
compare the identified repetition intervals and associated repetition patterns to reference data that is typical for sleep disordered breathing to extract the identified repetition intervals and associated repetition patterns that relate to sleep disordered breathing.

6. An apparatus as claimed in claim 5, wherein the reference data typical for sleep disordered breathing comprises breathing rate ranges typical for sleep disordered breathing.

7. An apparatus as claimed in claim 1, wherein the one or more processors are configured to:
analyze the identified repetition intervals and associated repetition patterns to segment the acquired acoustic signal into parts; and
for each part of the acquired acoustic signal:
identify a number of substantially different breathing patterns in the part; and
assign a label to the part, wherein the label is indicative of the identified number of substantially different breathing patterns in the part.

8. An apparatus as claimed in claim 7, wherein the one or more processors are configured to:
identify a part of the acquired acoustic signal corresponding to a disordered breathing episode for one subject; and
analyze at least one characteristic of the identified part of the acquired acoustic signal to identify the subject.

9. An apparatus as claimed in claim 8, wherein the one or more processors are configured to analyze the at least one characteristic of the identified part of the acquired acoustic signal by:
matching the at least one characteristic of the identified part of the acquired acoustic signal to at least one corresponding characteristic stored in a memory with an identity of a subject to which the at least one corresponding characteristic relates; and
identifying the subject as the subject to which the at least one corresponding characteristic relates.

10. An apparatus as claimed in claim 8, wherein the one or more processors are configured to:
analyze the identified part of the acquired acoustic signal to determine information on the sleep disordered breathing of the identified subject.

11. An apparatus as claimed in claim 1, wherein the sleep disordered breathing comprises any one or more of snoring, asthma, stridor, and apnea.

12. A method of operating a sound analysis apparatus for detecting a presence of multiple subjects in an environment with sleep disordered breathing, the method comprising:
acquiring an acoustic signal, via an acoustic sensor, in an environment;
determining, via one or more processors, a plurality of acoustic signal components from the acquired acoustic signal, the plurality of acoustic signal components differing from one another in respect of at least one signal characteristic or property;
determining, via the one or more processors, a plurality of signal envelopes or energy signals based on the acoustic signal components, where at least one signal envelope being derived from each of the acoustic signal components of the plurality of acoustic signal components;
analyzing, via the one or more processors, the determined plurality of signal envelopes or energy signals to detect whether there are one or more subjects in the environment with sleep disordered breathing, wherein the analyzing comprises identifying (i) a number of repetition patterns in the determined plurality of signal envelopes or energy signals and (ii) a repetition interval for each of the identified repetition patterns, and further comprises analyzing the number of repetition patterns and the repetition intervals to subdivide a time axis of a whole duration from a start to an end of a sound measurement of the acquired acoustic signal and provide an overview of sleep disordered breathing to be acquired for each subject, wherein the number of repetition patterns identified in each subdivided interval is indicative of a number of different subjects in the environment with sleep disordered breathing; and
rendering, via a user interface, information relating to sleep disordered breathing based on the detected one or more subjects in the environment with sleep disordered breathing, wherein the rendered information includes an identification of the detected one or more subjects and one or more characteristic of the detected sleep disordered breathing of a respective detected and identified subject.

13. A non-transitory computer readable medium having computer readable code embodied therein, the computer readable code being configured such that, on execution by a suitable computer or processor, the computer or processor is caused to perform the method as claimed in claim 12.

* * * * *